United States Patent [19]

Sharp

[11] Patent Number: 5,382,162
[45] Date of Patent: Jan. 17, 1995

[54] AUTOCLAVABLE DENTAL SCALER HANDPIECE SHEATH

[75] Inventor: Michael C. Sharp, Centerport, N.Y.

[73] Assignee: Parkell Products, Inc., Farmingdale, N.Y.

[21] Appl. No.: 147,642

[22] Filed: Nov. 4, 1993

[51] Int. Cl.⁶ ............................................. A61C 1/16
[52] U.S. Cl. ...................... 433/116; 433/119
[58] Field of Search ............... 433/86, 116, 119, 143

[56] References Cited

U.S. PATENT DOCUMENTS

| | | | |
|---|---|---|---|
| Re. 29,687 | 7/1978 | Sertich. | |
| 684,951 | 10/1901 | Rothkranz | 433/116 |
| 1,407,162 | 10/1923 | Gruss | 433/116 |
| 1,485,963 | 3/1924 | Curry | 433/116 |
| 1,517,186 | 11/1924 | Bond | 433/116 |
| 2,709,852 | 6/1955 | Maurer et al. | |
| 3,488,851 | 1/1970 | Haydu | 433/86 |
| 3,654,502 | 4/1972 | Carmona et al. | 433/119 |
| 4,110,908 | 9/1978 | Cranston | 433/143 |
| 4,403,956 | 9/1983 | Nakanishi | 433/29 |
| 4,619,612 | 10/1986 | Weber et al. | 433/80 |
| 4,757,381 | 7/1988 | Cooper et al. | 358/98 |
| 5,062,832 | 11/1991 | Seghi | 604/110 |
| 5,124,797 | 6/1992 | Williams et al. | 358/225 |

FOREIGN PATENT DOCUMENTS

| | | | |
|---|---|---|---|
| 695402 | 8/1953 | United Kingdom | 433/29 |

*Primary Examiner*—Cary E. O'Connor
*Attorney, Agent, or Firm*—Hoffmann & Baron

[57] ABSTRACT

An ultrasonic dental scaler device includes a handpiece having a removable outer sheath secured thereto. After performing a scaling procedure on a patient's teeth, the outer sheath is easily removed from the dental scaler handpiece and sterilized. A completely sterile sheath is secured to the dental scaler handpiece for use with each patient thereby preventing cross-contamination among different patients.

20 Claims, 3 Drawing Sheets

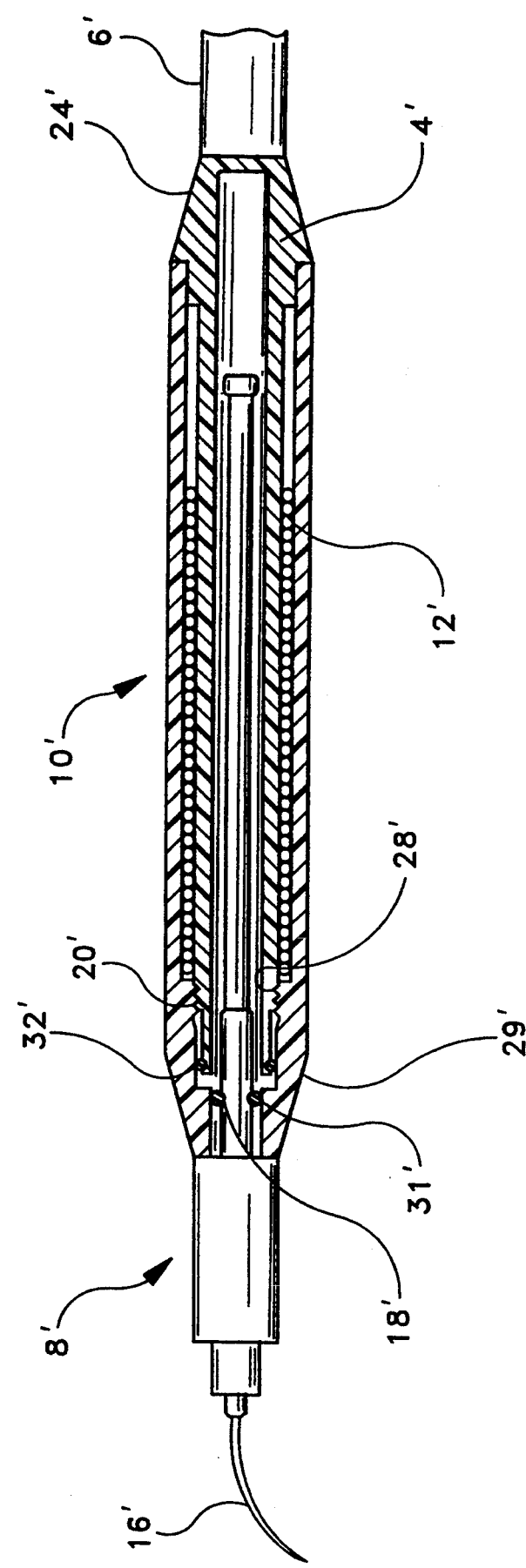

AUTOCLAVABLE DENTAL SCALER HANDPIECE SHEATH

BACKGROUND OF THE INVENTION

1. Field of the Invention

This invention relates to preventing cross-contamination when using a dental scaler device, and more particularly to sterilizing a dental scaler handpiece.

2. Description of the Prior Art

Dental scaler devices are known in the art for cleaning teeth. Generally, dental scaler devices vibrate a scaling tool at ultrasonic frequencies to facilitate the removal of calculus from a patient's teeth. Ultrasonic dental scalers usually comprise a handpiece adapted for receiving a dental scaler insert which includes a scaling tool, a flexible cable connecting the handpiece to a housing and the dental scaler device electronics contained within the housing. There are several different types of ultrasonic dental scaler devices including magnetostrictive scaling inserts and piezoelectric scaling inserts. For vibrating a magnetostrictive scaling insert, the handpiece generally includes an energizing coil which is positioned to surround a transducer of a magnetostrictivedental scaler insert placed within the handpiece of the scaler device. The magnetostrictive scaler insert generally comprises a transducer formed from a stack of laminar plates of magnetostrictive material that is excited by the energizing coil to longitudinally expand and contract at an ultrasonic frequency, such as about 25 kHz.

During the scaling procedure using conventional ultrasonic dental scaler devices, a patient's gums tend to bleed to some degree. Thus, when using dental tools such as a dental scaler, it is necessary to present to the patient a sterile surface. It is important that sterilized tools be used because bleeding will most likely occur during the scaling procedure, which presents a danger of transmission of Hepatitis-B and HIV, for example, if a contaminated dental scaler device is used. In the case of a dental scaler device, not only does the scaler insert require sterilization, but the handpiece of the device should also be sterilized since blood and saliva from a patient can easily come in contact with the handpiece.

Presently, scaler inserts are sterilizable by steam autoclaving which has been proven effective in preventing the transmission of Hepatitis-B and HIV. However, the handpiece of the conventional dental scalers are not designed to be autoclaved. Thus, the handpiece exterior surface is commonly cleaned by wiping the handpiece with a chemical sterilant. Simply wiping the exterior surface of the handpiece with a chemical sterilant is not considered to be acceptable practice for the prevention of the transmission of Hepatitis-B and HIV.

Other methods of sterilization such as ultra-violet (U.V.) irradiation are also available for sterilizing equipment such as dental scaler devices. U.V. irradiation has the disadvantage of taking a prolonged period of time to completely sterilize the equipment, thereby not allowing that particular piece of equipment to be readily reused with another patient. U.V. sterilization also has the disadvantage of not providing complete sterilization but only sterilizes those surfaces exposed to the U.V. irradiation. A common solution to this problem is the acquisition of numerous pieces of the same type of equipment, thereby allowing use of one instrument while others are being sterilized. For example, it is quite common for a dentist to have numerous dental mirrors and dental picks of the same type to be used while others are being sterilized. However, when the equipment requiring sterilization is an expensive, complex device, it is unlikely that a dentist will have more than one dental scaling unit. Thus, it is impractical to always sterilize a dental scaler handpiece.

Presently, dental scaler handpieces cannot be effectively and efficiently sterilized to prevent cross-contamination among patients.

OBJECTS AND SUMMARY OF THE INVENTION

It is an object of the present invention to provide a means for preventing cross-contamination among patients when using a dental scaler device.

It is a further object of the present invention to provide an ultrasonic dental scaler device having a sterilizable sheath removably positioned on the handpiece of the scaler device.

It is yet a further object of the present invention to provide an autoclavable dental scaler handpiece sheath removably positioned on the handpiece of the scaler device.

It is still a further object of the present invention to provide a method for sterilizing a dental scaler handpiece, which method overcomes the inherent disadvantages of known methods of sterilizing dental scaler handpieces.

In accordance with one form of the present invention, an ultrasonic dental scaler handpiece includes an elongated tubular inner housing having a proximal end coupled to a flexible cable and a distal end adapted for receiving a dental scaler insert. The dental scaler handpiece also includes a removable, elongated tubular outer sheath which is dimensioned to be selectively positioned around the inner housing. The outer sheath includes means for removably securing the sheath to the inner housing. After a dental scaling procedure is performed on a patient, the outer sheath may be removed from the dental scaler handpiece and sterilized thus preventing cross-contamination among patients. The dentist may have several outer sheaths available in his office so that a completely sterile sheath is always available for use with each patient.

The ultrasonic dental scaler device generally includes a handpiece adapted for receiving a dental scaler insert, an energizing coil mounted within the handpiece which surrounds a portion of a dental scaler insert positioned within the handpiece and an electronic circuit coupled to the energizing coil to provide power to the coil to vibrate a dental scaler positioned within the handpiece. As previously described, an outer sheath is positioned around the handpiece and is removably secured thereto. The outer sheath also protects the energizing coil and any other delicate electronics which is positioned within the dental scaler handpiece.

The outer sheath is preferably formed from a heat-resistant plastic such as an acetal resin or a polysulphone. Alternatively, in a piezoelectric ultrasonic dental scaling device, the outer sheath may be formed from a metal or an alloy. Furthermore, depending upon the material used to form the outer sheath, the sheath may be machined, molded or extruded into a suitable shape. A preferred shape includes a tubular portion fixedly coupled to a nosepiece having a frustoconical shape such that the tubular portion is coupled to the wider end of the nosepiece. This shape is designed to facilitate a smooth transitional assembly for ease of handling and use of the device.

Additionally, the device includes a cooperating securing means to removably secure the outer sheath to an ultrasonic dental scaler handpiece. The cooperating securing means may be in the form of mating threads positioned on the outer sheath and the dental scaler handpiece, although those skilled in the art will appreciate that any known cooperating securing means can be used. Furthermore, the securing means preferably includes means for making a water-tight seal at the point where the outer sheath is secured to the dental scaler handpiece. A typical seal for use with mating threads may be an O-ring seal, although other sealing means may be used.

The present invention is also directed to a method for preventing transmission of disease when using a dental scaler device which includes the steps of: providing a dental scaler handpiece having an outer sheath removably secured thereto, removing the outer sheath from the dental scaler handpiece after a scaling procedure is performed, sterilizing the outer sheath to kill any bacteria or virus which may be present on the outer sheath and securing a sterilized outer sheath onto a handpiece prior to using the dental scaler device with another patient. As previously mentioned, a preferred method of sterilizing the outer sheath includes steam autoclaving or alternatively by any other known sterilization method.

A preferred form of the ultrasonic dental scaler of the present invention, as well as other embodiments, objects, features and advantages of this invention, will be apparent from the following detailed description of illustrative embodiments thereof, which is to be read in conjunction with the accompanying drawings.

BRIEF DESCRIPTION OF THE DRAWINGS

FIG. 3 is a sectional view of a second embodiment of a dental scaler handpiece formed in accordance with the present invention.

DETAILED DESCRIPTION OF THE PREFERRED EMBODIMENTS

Figure 1:
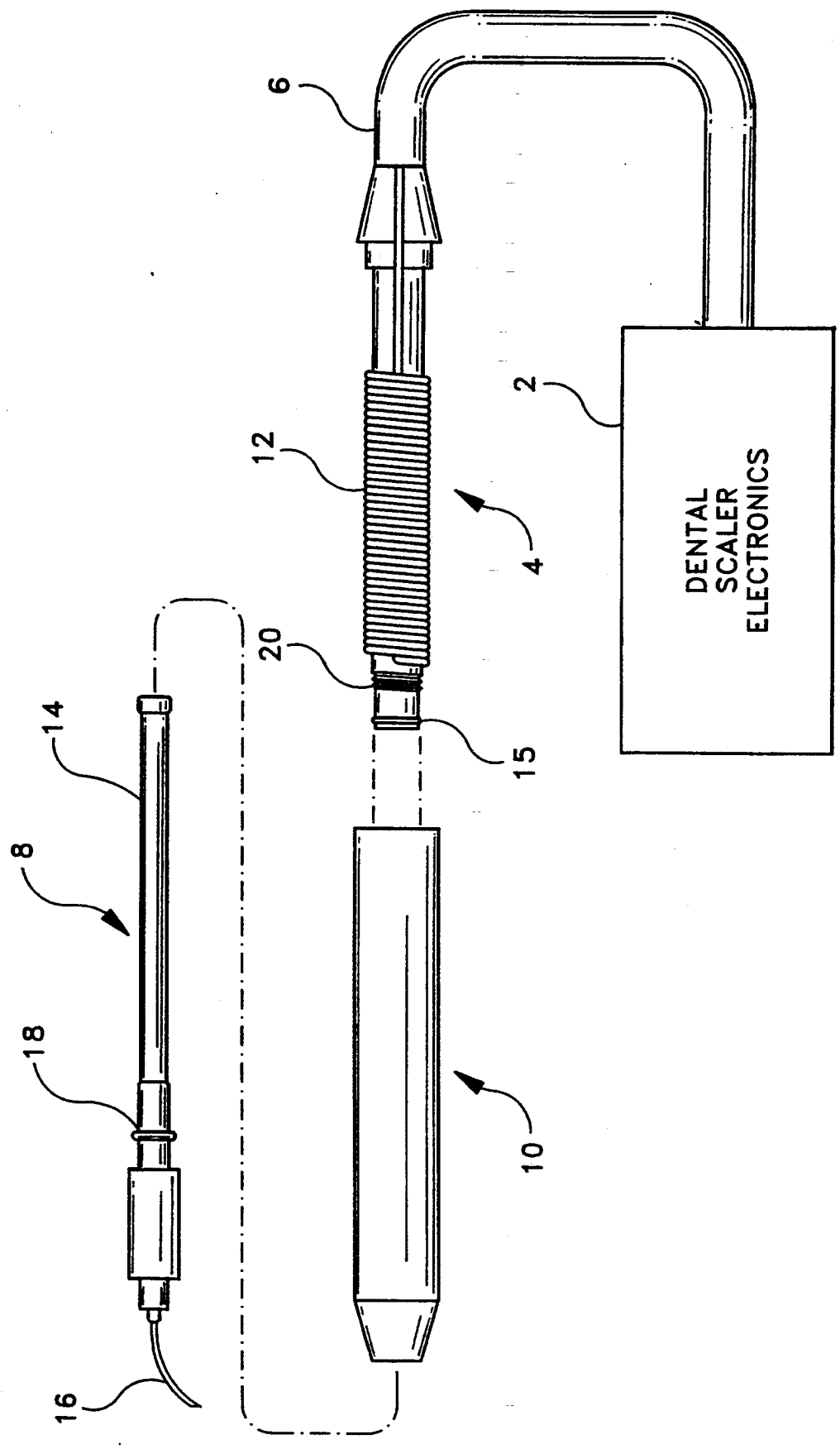
FIG. 1 is a side elevational view of an ultrasonic dental scaler device formed in accordance with the present invention, the handpiece of the scaler device being shown in an exploded view.

Referring to FIG. 1, a dental scaler formed in accordance with the present invention generally includes the dental scaler electronics 2 positioned within an enclosure, a handpiece including an inner housing 4 and a removable sheath 10, a flexible cable 6 coupling the handpiece to the dental scaler electronics and a dental scaler insert 8. The handpiece includes an opening extending into an axial bore at one end adapted to receive a dental scaler insert 8. The flexible cable 6 is attached to an opposite end of the handpiece.

Flexible cable 6 encloses a water hose (not shown) which delivers water for cooling the transducer of a magnetostrictive scaler. The water also serves as lavage to the handpiece of either a magnetostrictive or piezoelectric dental scaler device. In a magnetostrictive scaler device, the flexible cable 6 also encloses electrical wires which couple a coil 12 positioned on the handpiece to the dental electronics 2.

As shown in FIG. 1, the inner housing 4 of the handpiece of a magnetostrictive dental scaler device includes an energizing coil 12 wrapped around the exterior surface of the inner housing 4. Furthermore, the inner housing 4 includes a threaded portion 20 at its distal end adapted for receiving an internal mating thread positioned within the removable handpiece sheath. An O-ring seal 15 is provided near the tip of the distal end of the inner housing 4. The O-ring seal provides a water-tight connection between the outer sheath 10 and the lumen of the inner housing through which water flows and is discharged through a groove in the dental scaler insert for lavage. Alternative coupling and decoupling methods of securing the removable handpiece sheath to the inner housing 4, such as a spring loaded keyway which operates by pressing and twisting the sheath onto the inner housing, may be used. Thus, any known method of securing the sheath to the inner housing may be used without departing from the scope of the invention.

As is known in the art, a magnetostrictive scaler insert 8 comprises a transducer stack 14 which interacts with an alternating magnetic field created by the energizing coil 12 positioned in the handpiece to vibrate the scaler insert 8 at an ultrasonic frequency. The dental scaler electronics 2 controls the current supplied to the energizing coil 12 to vibrate the scaler insert 8 at its ultrasonic resonant frequency. The scaler insert 8 also includes a shaped dental tool 16 adapted to scale teeth. The dental tool 16 includes either a groove in the base of the tool or some other means such as a separate external tube arrangement for irrigating the work area while the dental scaling procedure is being performed. Furthermore, the scaler insert 8 includes an O-ring seal 18 for securely fitting and sealing the insert within the axial bore in the scaler handpiece.

Figure 2:
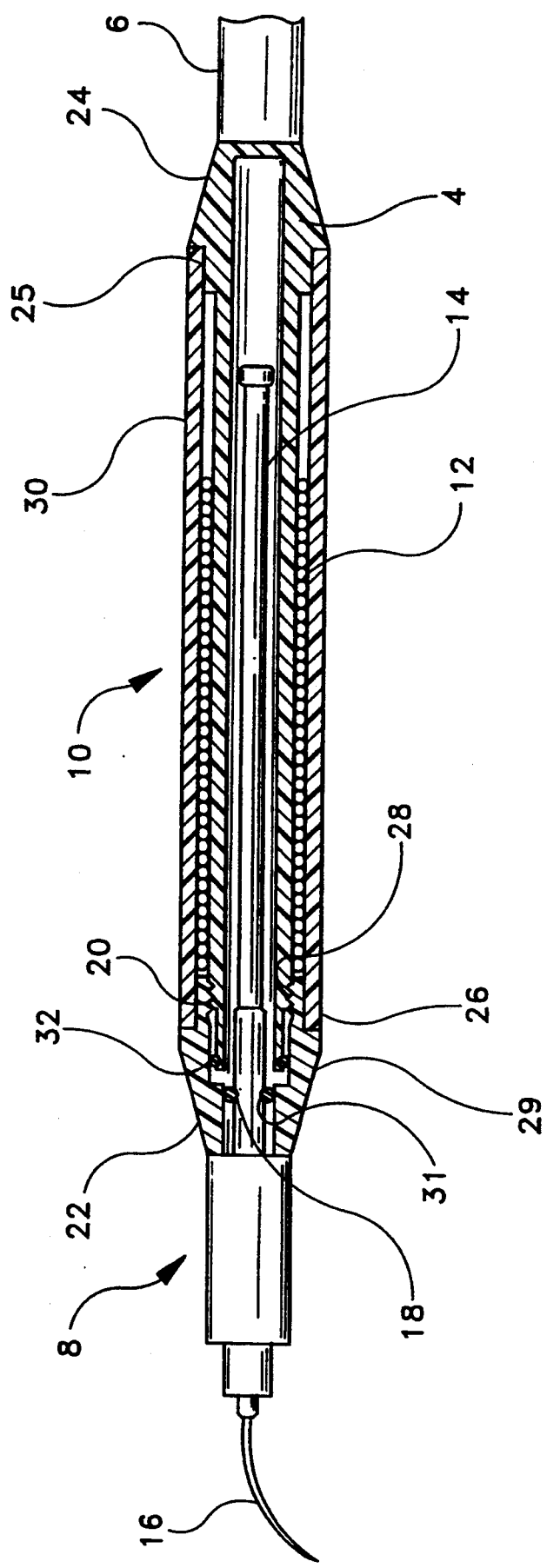
FIG. 2 is a sectional view of a first embodiment of a dental scaler handpiece formed in accordance with the present invention.

In a first embodiment formed in accordance with the present invention shown in FIG. 2, the dental scaler handpiece is illustrated with a scaler insert 8 positioned within the axial bore in the handpiece. As can be seen in FIG. 2, the outer diameter of the removable sheath 10 is greater than the opening in the handpiece adapted for receiving the scaler insert 8. Thus, in order to provide a smooth transition between the sheath 10 and scaler insert 8, the sheath 10 includes a nosepiece 22. The nosepiece 22 is generally a frustoconical body having a substantially similar diameter at a distal end to that of the scaler insert 8. At the proximal end of the nosepiece is an axially extending cylindrical portion 26 adapted for receiving a substantially tubular portion 30 of the handpiece sheath 10.

In this embodiment, the tubular portion 30 of the sheath is pre-assembled with the nosepiece 22 and friction-fitted to the axially extending cylindrical portion of the nosepiece 26. An inside surface of the axially extending cylindrical portion 26 of the nosepiece includes a threaded portion 28. The nosepiece 22 and tubular portion 30 are threadably secured onto the threaded portion 20 of the handpiece inner housing 4. This arrangement allows the sheath assembly 10 to be readily removed from the dental scaler handpiece for proper sterilization.

In a magnetostrictive ultrasonic scaler device, water is required to cool the transducer portion of the scaler insert when operating. Thus, water flows through the handpiece to cool the transducer and is expelled through a groove in the dental tool in the form of mist to irrigate the work area. Therefore, the device is provided with a sealing means such that water cannot migrate around the cooperating securing means which removably secures the outer sheath to the inner housing. In the embodiment shown in FIG. 2, the sealing means is an O-ring seal; however, any known sealing means may be used to provide a water-tight seal at the securing means without departing from the scope of the invention.

Referring to FIG. 2, the seal is accomplished by a tapered section 29 leading to a seal section 31 of the nosepiece 22 adapted for receiving the O-ring seal. The O-ring seal is positioned near the distal end of the inner housing as shown in FIG. 2. When the handpiece sheath 10 is threadably secured to the inner housing 4, the O-ring seal 32 is guided by the tapered section 29 into the sealing section 31 of the nosepiece to provide a water-tight seal to prevent any passage of materials or liquid onto the outer surface of the inner housing 4, including the energizing coil 12. The inner housing 4 may also include a piece of heat-shrinkable tubing (not shown) which is fitted over the energizing coil to protect the coil when the outer sheath is removed and replaced.

The sealing section 31 which is adapted for receiving the O-ring seal 32 positioned on the distal end of the inner housing is sufficiently sized to permit the handpiece sheath 10 to be loosely secured to the inner housing, yet still provide a water-tight seal. Thus, a seal is effected when the O-ring 32 contacts any portion of the sealing section 31. In this manner, a positive seal is accomplished without concern whether the sheath 10 is completely threaded onto the inner housing 4 of the handpiece.

The proximal end 24 of the handpiece which is coupled to the flexible cable 6 also includes a generally frustoconical shape to provide a smooth transition of the handpiece into the flexible cable. The frustoconical proximal end 24 of the handpiece includes an axial extending cylindrical portion 25 adapted for receiving the handpiece sheath tubular portion 30. The handpiece sheath tubular portion is removably friction-fitted onto the axial extending cylindrical portion 25 at the proximal end of the handpiece.

An alternative embodiment of the dental scaler handpiece sheath is illustrated in FIG. 3 such that like parts are numbered with like reference numerals having a superscript. In this embodiment, the handpiece sheath 10' is a single, integrally formed sheath. The separate nosepiece and tubular section previously described are molded or machined in a single, integrally formed sheath 10' which is removably secured to the inner housing 4' of the scaler handpiece. More specifically, the inner housing 4' and integrally formed outer sheath 10' have mating threads 28' thereon to threadably secure the outer sheath to the handpiece.

The integrally formed handpiece sheath 10' also includes a water-tight sealing means so that water passing through the handpiece cavity does not contact the energizing coil 12' positioned on the inner housing 4' of the handpiece or leak from the handpiece. The sealing means is an O-ring seal 32' positioned such that when the outer sheath 10' is threaded onto the inner housing 4' the O-ring contacts a tapered section 29' of the sheath to provide a water-tight seal. As previously mentioned, the tapered section 29' of the sheath permits a positive seal to be effected even if the handpiece sheath 10 were loosely secured in the inner housing 4'. In this way, an allowance for tolerances in the fitting of the outer sheath to the inner housing does not effect the seal created therebetween.

Similar to the first embodiment shown in FIG. 2, the second embodiment shown in FIG. 3 includes an axial bore through the handpiece for receiving a dental scaler insert 8'. The proximal end of the scaler handpiece includes a frustoconical shaped section 24' to provide a smooth transition of the handpiece into the flexible cable 6'. Naturally, the handpiece is preferably shaped to facilitate ease of handling during a dental scaling procedure. Thus, the handpiece sheath 10' may be shaped with contours (not shown) conforming to the shape of an operator's hand.

Those skilled in the art will appreciate that the removable sheath for use with a dental scaler device formed in accordance with the present invention may be formed in any number of ways. The dental scaler device includes any suitable coupling means for removably securing the sheath to the dental scaler handpiece and any sealing means without departing from the scope of the invention.

During operation of the dental scaler device formed in accordance with the present invention, the scaler tool 16 is vibrated at an ultrasonic frequency for cleaning the surface of a patient's teeth. During the cleaning procedure, most patients will, to some degree, bleed from the gums. The patient's blood and saliva is, in most cases, sprayed by the ultrasonically vibrating scaler tool onto the hand of the dentist as well as the handpiece of the scaler device. As previously described in the Background of the Invention, it is common for dentists to clean the scaler handpiece by simply wiping a chemical sterilant onto the surface of the handpiece. Chemical sterilants are not always considered to be an acceptable method of preventing cross-contamination among patients and for preventing the spread of Hepatitis-B and HIV.

Thus, a dental scaler device formed in accordance with the present invention provides a removable sheath 10 selectively secured to an inner housing 4 of the dental scaler handpiece. The removable sheath 10 is sterilizable by a number of sterilization techniques including but not limited to soaking in chemical sterilants, U.V. irradiation, ethylene oxide sterilization and most preferably sterilized by steam autoclaving. Previous dental scaler handpieces could not be steam autoclaved since the handpiece generally includes delicate electronics, wiring and electrical connections which could not be subjected to the extreme heat and moisture of a steam autoclave. Alternatively, those scalers having removable handpieces generally included plastics which could not withstand autoclaving. Furthermore, prolonged methods of sterilization such as U.V. irradiation prevent operation of the dental scaler with another patient for a prolonged period of time or did not provide complete sterilization.

The dental scaler handpiece formed in accordance with the present invention is particularly well suited for steam autoclaving. The handpiece includes a removable sheath 10 preferably made from a heat-resistant plastic and more preferably made from an acetal resin such as DELRIN, manufactured by DuPont, or a synthetic thermoplastic polymer such as polysulphone. The removable handpiece sheath 10 may be machined, molded or extruded into a suitable shape depending upon the heat-resistant plastic chosen to form the sheath. A design consideration when forming the outer sheath 10 from a thermoplastic, and especially DELRIN, is that the sheath and particularly the threaded portion thereof tends to shrink when autoclaved. To compensate for shrinkage, the threads are designed to be originally slightly oversized. Following autoclaving, the threads shrink to a desired size. The sealing means previously described also compensates for an initially oversized sheath by creating an effective water-tight seal with its unique design. Alternatively, in a piezoelectronic ultrasonic scaler, the dental scaler outer sheath may be formed from a metal or alloy which may be specifically shaped to facilitate ease of handling in use.

In general, the dental scaler device formed in accordance with the present invention will include several interchangeable removable handpiece sheaths so that the scaler device may be used while a previously used sheath is being sterilized. In this manner, the dentist always has available a sterilized dental scaler ready for use with a patient.

The present invention is also directed to a method of sterilizing a dental scaler handpiece to prevent cross-contamination among patients. The method in accordance with the present invention includes the steps of assembling the dental scaler handpiece by readily and easily securing a sterilized outer sheath to the scaler handpiece, performing a dental scaling procedure to clean calculus from teeth surfaces, readily removing the dental scaler handpiece sheath from the device, sterilizing the scaler handpiece sheath preferably using a steam autoclave to prevent cross-contamination among patients and securing a sterilized dental scaler handpiece sheath onto the dental scaler handpiece so that the scaler device can be safely used with another patient. The outer sheath is designed to be easily coupled to and disassembled from the dental scaler handpiece to facilitate sterilizing. By providing a dental scaler device having the capability to remove and sterilize the outer sheath which provides protection to the components of the handpiece, the operator of the dental scaler device can ensure that a completely sterile instrument is being used with each patient.

Thus, the dental scaler device having a removable handpiece sheath formed in accordance with the present invention provides a method for sterilizing a dental scaler handpiece to prevent cross-contamination among patients. More specifically, the sheath is easily removable from the dental scaler handpiece to permit sterilization of the removable sheath which is contaminated by a patient's saliva and blood during a scaling procedure. The dental scaler device having a readily removable and replaceable sterilizable outer sheath provides an improved method and apparatus for performing dental scaling procedures. The dental scaler handpiece formed in accordance with the present invention overcomes the disadvantages of the prior art devices by providing a completely sterile dental scaler handpiece for use with each patient.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An ultrasonic dental scaler handpiece adapted for receiving a dental scaler insert comprising:
   a removable, protective, elongated outer sheath dimensioned to be selectively positioned around said scaler handpiece, the outer sheath being shaped to facilitate gripping by an operator; and
   coupling means for removably securing said outer sheath to said scaler handpiece such that when said outer sheath is removed from said scaler handpiece, the outer sheath is sterilizable to prevent cross-contamination among patients, said coupling means being provided on surfaces substantially independent of an exposed outer surface of said outer sheath thereby maintaining a substantially continuous gripping shape.

2. An ultrasonic dental scaler handpiece as defined by claim 1, wherein said outer sheath comprises a heat-resistant plastic.

3. An ultrasonic dental scaler handpiece as defined by claim 2, wherein said heat-resistant plastic is an acetal resin.

4. An ultrasonic dental scaler handpiece as defined by claim 2, wherein said heat-resistant plastic is polysulphone.

5. An ultrasonic dental scaler handpiece as defined by claim 1, wherein said outer sheath comprises a machined, heat-resistant plastic.

6. An ultrasonic dental scaler handpiece as defined by claim 1, wherein said outer sheath comprises a molded, heat-resistant plastic.

7. An ultrasonic dental scaler handpiece as defined by claim 1, wherein said outer sheath is sterilizable by steam autoclaving.

8. An ultrasonic dental scaler handpiece as defined by claim 1, wherein the outer sheath comprises metal.

9. An ultrasonic dental scaler handpiece as defined by claim 1, wherein said outer sheath comprises a nosepiece having a frustoconical shape and a tubular portion fixedly coupled to a wider end of said nosepiece.

10. An ultrasonic dental scaler handpiece as defined by claim 1, wherein the coupling means comprises an internally positioned releasable coupling system.

11. An ultrasonic dental scaler handpiece adapted for receiving a dental scaler insert comprising:
    a removable, protective, elongated outer sheath dimensioned to be selectively positioned around said scaler handpiece, the outer sheath being shaped to facilitate gripping by an operator; and
    coupling means for removably securing said outer sheath to said scaler handpiece such that when said outer sheath is removed from said scaler handpiece, the outer sheath is sterilizable to prevent cross-contamination among patients, wherein said coupling means comprises mating threads for threadably securing said outer sheath to said dental scaler handpiece.

12. An ultrasonic dental scaler handpiece adapted for receiving a dental scaler insert comprising:
    a removable, protective, elongated outer sheath dimensioned to be selectively positioned around said scaler handpiece, the outer sheath being shaped to facilitate gripping by an operator; and
    coupling means for removably securing said outer sheath to said scaler handpiece such that when said outer sheath is removed from said scaler handpiece, the outer sheath is sterilizable to prevent cross-contamination among patients, wherein said coupling means includes means for making a water-tight seal between said outer sheath and dental scaler handpiece.

13. An ultrasonic dental scaler comprising:

a handpiece adapted for receiving a magnetostrictive dental scaler insert;

an energizing coil mounted within said handpiece such that said energizing coil surrounds a portion of a magnetostrictive dental scaler insert positioned within said handpiece;

an electronic circuit coupled to said energizing coil which provides current to said energizing coil to vibrate a dental scaler positioned within said handpiece; and an outer sheath positioned around said handpiece and including coupling means for removably securing the outer sheath thereto whereby upon removal of said outer sheath, said outer sheath is sterilizable to prevent cross-contamination among patients and wherein the coupling means is provided on surfaces substantially independent of an exposed outer surface of said outer sheath thereby providing a substantially continuous gripping shape.

14. An ultrasonic dental scaler as defined by claim 13, wherein said outer sheath comprises a heat-resistant plastic.

15. An ultrasonic dental scaler as defined by claim 14, wherein said heat-resistant plastic is a synthetic thermoplastic polymer.

16. An ultrasonic dental scaler as defined by claim 13, wherein said outer sheath is autoclavable.

17. An ultrasonic dental scaler as defined by claim 13, wherein the coupling means includes a sealing means to effect a water-tight seal between said outer sheath and said dental scaler handpiece.

18. An ultrasonic dental scaler comprising:

a handpiece adapted for receiving a magnetostrictive dental scaler insert;

an energizing coil mounted within said handpiece such that said energizing coil surrounds a portion of a magnetostrictive dental scaler insert positioned within said handpiece;

an electronic circuit coupled to said energizing coil which provides current to said energizing coil to vibrate a dental scaler positioned within said handpiece; and an outer sheath positioned around said handpiece and being removably secured thereto whereby said outer sheath is sterilizable to prevent cross-contamination among patients and wherein the handpiece includes an elongated, tubular inner housing and said outer sheath is threadably secured to said inner housing of the handpiece.

19. A method for preventing transmission of disease when using a dental scaler device comprising the steps of:

providing a dental scaler handpiece comprising a removable, protective, elongated outer sheath dimensioned to be selectively positioned around said scaler handpiece, the outer sheath being shaped to facilitate gripping by an operator and coupling means for removably securing said outer sheath to said scaler handpiece and wherein the coupling means is provided on surfaces substantially independent of an exposed outer surface of said outer sheath thereby maintaining a substantially continuous gripping shape;

assembling the dental scaler handpiece to include the outer sheath secured thereto;

performing a dental scaling procedure using said dental scaler device to clean calculus from teeth surfaces;

disassembling the dental scaler handpiece by removing the outer sheath from the dental scaler handpiece after said scaling procedure is performed;

sterilizing the outer sheath removed from the dental scaler to prevent cross-contamination among patients and;

reassembling the dental scaler handpiece by securing a sterilized outer sheath onto said handpiece prior to using the dental scaler device with another patient.

20. A method as defined by claim 19, wherein the step of sterilizing the outer sheath includes the step of steam autoclaving the outer sheath.

* * * * *